United States Patent
Clark et al.

(10) Patent No.: US 11,707,433 B2
(45) Date of Patent: Jul. 25, 2023

(54) METHODS AND COMPOSITIONS FOR TREATING DIABETIC FOOT ULCERS

(71) Applicant: Pathway Development, LLC, Madison, MS (US)

(72) Inventors: Jeffrey Clark, Madison, MS (US); Jeffery King, Madison, MS (US)

(73) Assignee: PATHWAY DEVELOPMENT LLC, Madison, MS (US)

(*) Notice: Subject to any disclaimer, the term of this patent is extended or adjusted under 35 U.S.C. 154(b) by 123 days.

(21) Appl. No.: 17/009,509

(22) Filed: Sep. 1, 2020

(65) Prior Publication Data

US 2021/0059934 A1 Mar. 4, 2021

Related U.S. Application Data

(60) Provisional application No. 62/894,826, filed on Sep. 1, 2019.

(51) Int. Cl.
| | | |
|---|---|---|
| *A61K 9/08* | (2006.01) | |
| *A61K 31/7036* | (2006.01) | |
| *A61K 31/4725* | (2006.01) | |
| *A61K 38/14* | (2006.01) | |
| *A61K 31/497* | (2006.01) | |
| *A61K 31/4174* | (2006.01) | |
| *A61M 3/02* | (2006.01) | |

(52) U.S. Cl.
CPC ............ *A61K 9/08* (2013.01); *A61K 31/4174* (2013.01); *A61K 31/4725* (2013.01); *A61K 31/497* (2013.01); *A61K 31/7036* (2013.01); *A61K 38/14* (2013.01); *A61M 3/0204* (2014.02); *A61M 3/0229* (2013.01)

(58) Field of Classification Search
CPC .. A61K 31/4725; A61K 31/7036; A61K 9/08; A61K 9/0014; A61K 31/497; A61K 31/4174; A61K 38/14; A61M 3/0204; A61M 3/0229

See application file for complete search history.

(56) References Cited

U.S. PATENT DOCUMENTS

| | | | |
|---|---|---|---|
| 2006/0235350 A1* | 10/2006 | Alimi | A61K 33/20 604/19 |
| 2011/0213320 A1* | 9/2011 | Blott | A61M 1/915 604/313 |
| 2018/0071238 A1* | 3/2018 | Li | A61K 45/06 |
| 2019/0290736 A1* | 9/2019 | Buice | A61K 9/006 |

* cited by examiner

*Primary Examiner* — Jianfeng Song
(74) *Attorney, Agent, or Firm* — Perilla Knox & Hildebrandt LLP; Thomas B. Hildebrandt

(57) ABSTRACT

In one aspect, the disclosure relates to methods and compositions, i.e., pharmaceutical formulations, for treating and preventing diabetic foot ulcers. In a particular aspect, the disclosed methods and compositions pertain to water-based pharmaceutical formulations that are useful for administration in an aqueous foot bath. This abstract is intended as a scanning tool for purposes of searching in the particular art and is not intended to be limiting of the present disclosure.

15 Claims, No Drawings

METHODS AND COMPOSITIONS FOR TREATING DIABETIC FOOT ULCERS

CROSS-REFERENCE TO RELATED APPLICATIONS

This application claims the benefit of U.S. Provisional Application Ser. No. 62/894,826, filed Sep. 1, 2019, which is incorporated herein by reference in its entirety.

FIELD

The present disclosure relates to methods and compositions for treating diabetic foot ulcers.

BACKGROUND

Diabetes is a chronic disease where the body is unable to control blood glucose due to defects in insulin secretion, insulin action or both. Diabetes may lead to a number of complications, resulting from damage exerted by hyperglycemia (blood glucose increases above normal levels) to organs and systems, especially to nerves and blood vessels.

In the U.S., diabetes has reached epidemic proportions. According to a recent report from the United States Centers for Disease Control and Prevention (CDC), more than 100 million U.S. adults are now living with diabetes or prediabetes. The report finds that as of 2015, 30.3 million Americans—9.4 percent of the U.S. population—have diabetes. Another 84.1 million have prediabetes, a condition that if not treated often leads to type 2 diabetes within five years. The prevalence is particularly striking in older populations, with the percentage of Americans age 65 and older remains estimated at 25.2%, or 12.0 million seniors (diagnosed and undiagnosed). According to data from the American Diabetes Association, about 1.5 million new cases are diagnosed in the United States each year.

Diabetes puts tremendous economic pressure on the U.S. healthcare system, e.g., total costs (direct and indirect) of diabetes have reached $327 billion annually (as of 2017 data from the American Diabetes Association), which includes $237 billion for direct medical costs and at least $90 billion related to reduced productivity in the population affected. People with diagnosed diabetes have medical expenditures that are over two times higher than medical expenditures for people without diabetes. Hospitalization costs alone are $16,000 to $20,000 for a patient with a diabetic foot ulcer, and direct and indirect costs of an amputation range from $20,000 to $60,000 per patient for the initial year with an additional 40,000 to 70,000 spent over the next 3 years.

Diabetic foot ulcers are chronic and complex wounds which use to be a result from one or more simultaneously caused risk factors. One such risk factor is peripheral neuropathy, defined as a loss of protective sensitivity such as pain and autonomic dysfunction. Other risk factors are peripheral arterial disease, increased levels of glycosylated hemoglobin, decrease of visual acuity, record of ulcer or amputation and onychomycosis. External trauma is an instrumental component for ulcer development having as main origin the use of unsuitable footwear.

It is less frequent that peripheral vascular disease is the precipitating event of diabetic foot ulcers; however, it plays an essential role in wound healing and in gangrene development; it is a contributing factor for half of amputations. Although the instrumental or triggering event of ulcer is frequently external trauma, the peripheral vascular disease is the underlying basis of physiopathology of this diabetic foot complication. Even when ulcer pathogenesis is neuropathy, a vascular etiology has been proposed for neuropathy.

Diabetic ulcers show amputation of affected limbs as a main problem; being demonstrated that 85% of lower limb amputations in diabetic patients are preceded by ulcerations, which allow entry of infectious agents, thus causing progressive tissue necrosis with minimum wound healing in the presence of ischemic media.

Amputation rate in diabetic patients is 15 times higher compared to general population. Moreover, it has been noticed that in 58% of patients who have suffered any amputation resulting from diabetic ulcers, there will be a new amputation in their opposite lower limb within the following 3 to 5 years; while mortality within 2 years after the first amputation is of 20 to 50%.

Importantly, up to 25% of people with diabetes will develop a diabetic foot ulcer, resulting in 3 million diabetic foot ulcers annually in the U.S. alone. More than half of all foot ulcers will become infected, thus requiring hospitalization, and 1 in 5 will require an amputation that carries a high risk of mortality. Diabetic foot ulcers and other foot complications cause 20% of all hospitalizations for diabetic patients each year.

Despite advances in research directed to diabetes and its co-morbidities, including diabetic foot ulcers, there remains a great need for cost-effective and patient friendly modalities for the treatment of diabetic foot ulcers. These needs and other needs are satisfied by the present disclosure.

SUMMARY

In accordance with the purpose(s) of the present disclosure, as embodied and broadly described herein, the disclosure, in one aspect, relates to pharmaceutical formulations as disclosed herein, irrigation therapy solutions comprising the disclosed pharmaceutical formulations, and methods of use the disclosed irrigation therapy solutions.

Disclosed are pharmaceutical compositions comprise: a first antimicrobial agent, a second antimicrobial agent, a third antimicrobial agent, and a powder excipient base; wherein the first antimicrobial agent is an aminoglycoside antibiotic or a fluoroquinolone antibiotic, and is present in an amount of from about 15 wt % to about 35 wt %; wherein the second antimicrobial agent is glycopeptide antibiotic, and is present in an amount of from about 15 wt % to about 40 wt %; wherein the third antimicrobial agent is an azole antifungal or an imidazole antifungal, and is present in an amount of from about 1 wt % to about 15 wt %; wherein the powder excipient base is present in an amount of from about 10 wt % to about 50 wt %; wherein the wt % is based on the total weight of the first antimicrobial agent, the second antimicrobial agent, the third antimicrobial agent, and the powder excipient base such that the total wt % for foregoing components is 100 wt %; and wherein the first antimicrobial agent, the second antimicrobial agent, the third antimicrobial agent, and the powder excipient base are a homogeneously dispersed powder mixture.

Also disclosed are irrigation therapy compositions comprising about 1 gram to about 10 grams of a disclosed pharmaceutical composition dissolved in a volume of about 1.5 to about 5 liters of water.

Also disclosed are methods for the treatment of diabetic foot ulcers, comprising administering to a subject an effective amount of a disclosed irrigation therapy solution, wherein the subject is diagnosed with diabetes; wherein the disclosed irrigation therapy solution is contained in a suitable irrigation therapy delivery device; and wherein administering comprises the subject placing at least one foot in the irrigation therapy delivery device for a suitable period of time.

Also disclosed are kits comprising a disclosed pharmaceutical formulation; and one or more of: (a) instructions for treating a diabetic foot ulcer; (b) instructions for preventing a diabetic foot ulcer; (c) instructions for preparation of an irrigation therapy solution for treating a diabetic foot ulcer; (d) instructions for preparation of an irrigation therapy solution for preventing a diabetic foot ulcer; or (e) an irrigation therapy delivery device for circulating an aqueous solution comprising the pharmaceutical formulation for use in treating or preventing a diabetic foot ulcer.

Also disclosed are kits comprising a disclosed irrigation therapy solution; and one or more of: (a) instructions for treating a diabetic foot ulcer; (b) instructions for preventing a diabetic foot ulcer; or (c) an irrigation therapy delivery device for circulating an aqueous solution comprising the pharmaceutical formulation for use in treating or preventing a diabetic foot ulcer.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described aspects are usable in all aspects of the disclosure taught herein. Furthermore, the individual features of the dependent claims, as well as all optional and preferred features and modifications of the described aspects are combinable and interchangeable with one another.

DETAILED DESCRIPTION

Many modifications and other aspects disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific aspects disclosed and that modifications and other aspects are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual aspects described and illustrated herein has discrete components and features which may be readily separated from or combined with the features of any of the other several aspects without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior disclosure. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of".

As used herein, the term "and/or" includes any and all combinations of one or more of the associated listed items. Expressions such as "at least one of," when preceding a list of elements, modify the entire list of elements and do not modify the individual elements of the list.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

Reference to "a" chemical compound or pharmaceutical agent, such as a drug, refers to one or more molecules of the chemical compound or pharmaceutical agent rather than being limited to a single molecule of the chemical compound. Furthermore, the one or more molecules may or may not be identical, so long as they fall under the category of the chemical compound. Thus, for example, "a" chemical compound is interpreted to include one or more molecules of the chemical, where the molecules may or may not be identical (e.g., different isotopic ratios, enantiomers, and the like).

As used in the specification and the appended claims, the singular forms "a," "an" and "the" include plural referents unless the context clearly dictates otherwise. Thus, for example, reference to "an ulcer," "a dose," or "a treatment," including, but not limited to, two or more such ulcers, doses, treatments, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a drug, e.g., a disclosed antimicrobial agent refers to an amount that is sufficient to achieve the desired improvement in a clinically useful parameter, e.g. increased rate of wound healing compared to conventional treatment. The specific level in terms of dose, e.g., concentration of the antimicrobial in an aqueous treatment solution, in a formulation required as an effective amount will depend upon a variety of factors including the type of infection, other existing co-morbidities in the subject treated, age of the subject treated, and nature of prior treatments for condition associated with the treated diabetic ulcer.

As used herein the terms "weight percent," "wt %," and "wt. %," which can be used interchangeably, indicate the percent by weight of a given component based on the total weight of the composition, unless otherwise specified. That is, unless otherwise specified, all wt % values are based on the total weight of the composition. It should be understood that the sum of wt % values for all components in a disclosed composition or formulation are equal to 100.

As used herein, the terms "optional" or "optionally" means that the subsequently described event or circumstance can or cannot occur, and that the description includes instances where said event or circumstance occurs and instances where it does not.

As used herein, "administering" can refer to an administration that as disclosed herein, e.g., immersion of an affected area of the body in a disclosed formulation or solution, providing a wound dressing comprising a disclosed formulation or solution, or topically administering a disclosed formulation or solution. Administration can be continuous or intermittent. In various aspects, a preparation can be administered therapeutically; that is, administered to treat an existing disease or condition. In further various aspects, a disclosed formulation or solution can be administered prophylactically; that is, administered for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as a chronic wound or ulcer. The effect can be therapeutic in terms of a partial or complete cure of a disease, condition, symptom or adverse effect attributed to the disease, disorder, or condition. The term "treatment" as used herein can include any treatment of a wound, e.g., a chronic wound, or ulcer in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units, e.g., blister packs or amounts such as a volume, weight, or mass, suitable for use in a subject, each unit containing a predetermined quantity of a disclosed pharmaceutical formulation or a disclosed solution thereof calculated to produce the desired response or responses in association with its administration.

As used in present disclosure, the term "conventional treatment" considers ambulatory wound care, application of antibiotics when needed, use of membranes and healing creams wet to dry dressings, and oral or IV antibiotics.

As used herein, "Dakin's solution" refers to an aqueous solution comprising 0.5% sodium hypochlorite containing about 5000 ppm free chlorine.

As used herein, the terms "antimicrobial agent", "antibacterial agent", "antibiotic agent" and "bactericidal agent" are used interchangeably.

As used herein, the term "antiseptic" refers to a substance or agent suitable for topical use (i.e., such as benzalkonium chloride or sodium hypochlorite) that prevents or arrests the growth of microorganisms (e.g., bacteria, viruses and fungi) in a skin wound, burn, or other skin injury. The prevention or arresting of growth of microorganisms can be either by inhibiting activity and/or growth or by destroying (killing) the microorganisms.

Unless otherwise specified, temperatures referred to herein are based on atmospheric pressure (i.e. one atmosphere) and are based on the Celsius scale Pharmaceutical Formulations for Treatment of Diabetic Foot Ulcers Disclosed herein are pharmaceutical formulations for the treatment and/or prevention of diabetic foot ulcers. The disclosed pharmaceutical formulations are prepared as a powder for use in an irrigation therapy solution. In further aspects, the disclosed pharmaceutical formulations can be utilized to prepare a solution, e.g., an aqueous solution, for use as an antimicrobial spray or to apply to a wound dressing prior to application of the wound dressing to a wound.

In various aspects, the disclosed pharmaceutical compositions comprise: a first antimicrobial agent, a second antimicrobial agent, a third antimicrobial agent, and a powder excipient base; wherein the first antimicrobial agent is an aminoglycoside antibiotic or a fluoroquinolone antibiotic, and is present in an amount of from about 15 wt % to about 35 wt %; wherein the second antimicrobial agent is glycopeptide antibiotic, and is present in an amount of from about 15 wt % to about 40 wt %; wherein the third antimicrobial agent is an azole antifungal or an imidazole antifungal, and is present in an amount of from about 1 wt % to about 15 wt %; wherein the powder excipient base is present in an amount of from about 10 wt % to about 50 wt %; wherein the wt % is based on the total weight of the first antimicrobial agent, the second antimicrobial agent, the third antimicrobial agent, and the powder excipient base such that the total wt % for foregoing components is 100 wt %; and wherein the first antimicrobial agent, the second antimicrobial agent, the third antimicrobial agent, and the powder excipient base are a homogeneously dispersed powder mixture.

In a further aspect, the amino glycoside antibiotic can be selected from gentamicin, tobramycin, dibekacin, amikacin, netilimicin, streptomycin, neomycin, including neomycin B and/or neomycin C, arbekacin, spectinomycin, verdamicin, astromicin, sisomicin, paromomycin, framycetin, geneticin, bekanamycin, ribostamycin, isepamicin, or a pharmaceutically acceptable salt thereof. In a still further aspect, the amino glycoside antibiotic is tobramycin, or a pharmaceutically acceptable salt thereof.

In a further aspect, the fluoroquinolone antibiotic can be selected from ciprofloxacin (Cipro), balofloxacin (Baloxin), cinoxacin (Cinobac), clinafloxacin, danofloxacin (Advocin, Advocid), delafloxacin, difloxacin (Dicural, Vetequinon), enoxacin (Enroxil, Penetrex), enrofloxacin (Baytril), fleroxacin (Megalone, Roquinol), flumequine (Flubactin), garenoxacin (Geninax), gatifloxacin (Tequin, Zymar), gemifloxacin (Factive), grepafloxacin (Raxar), ibafloxacin (Ibaflin), levofloxacin (Cravit, Levaquin), lomefloxacin (Maxaquin), marbofloxacin (Marbocyl, Zenequin), moxifloxacin (Avelox, Vigamox), nadifloxacin (Acuatim, Nadoxin, Nadixa), nalidixic acid (NegGam, Wintomylon), norfloxacin (Lexinor, Noroxin, Quinabic, Janacin), ofloxacin (Floxin, Oxaldin, Tarivid), orbifloxacin (Orbax, Victas), oxolinic acid (Uroxin), pazufloxacin (Pasil, Pazucross), pefloxacin (Peflacine), pipemidic acid (Dolcol), piromidic acid (Panacid), prulifloxacin (Quisnon), rosoxacin (Eradacil), rufloxacin (Uroflox), sarafloxacin (Floxasol, Saraflox, Sarafin), sitafloxacin (Gracevit), sparfloxacin (Zagam), temafloxacin (Omniflox), tosufloxacin (Ozex, Tosacin) and trovafloxacin (Trovan). In a still further aspect, the fluoroquinolone antibiotic is ciprofloxacin, or a pharmaceutically acceptable salt thereof.

In a further aspect, the glycopeptide antibiotic can be selected from vancomycin (oritavancin, telavancin), teicoplanin (dalbavancin) and ramoplanin. In a still further aspect, the glycopeptide antibiotic is vancomycin, or a pharmaceutically acceptable salt thereof. As used herein, "glycopeptide antibiotic" means molecules which contain a heptapeptide structure providing specific affinity for the D-alanyl-D-Alanine terminus of the peptidoglycan pentapeptide including, for example, vancomycin, telavancin, oritavancin, teicoplanin and dalbavancin (See Parenti & Cavallieri, Journal of Antibiotics, December 1989 page 1882). Vancomycin is a tricyclic glycopeptide antibiotic. Its structure is represented in Formula 1. Its purity in the formulation can be assessed by the content of Vancomycin B. "Vancomycin" as used herein means the compound represented in Formula 1 and also pharmaceutically acceptable salts thereof, for example Vancomycin Hydrochloride.

Formula 1

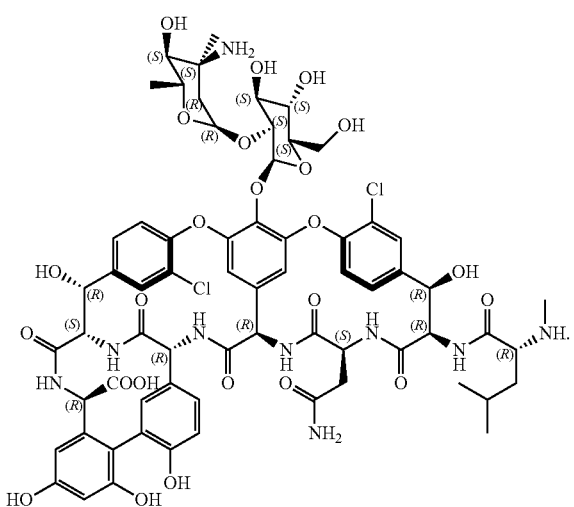

In a further aspect, the azole antifungal can be selected from butoconazole, clotrimazole, terconazole, econazole, tioconazole, fluconazole, elubiol, ketoconazole and itraconazole. In a still further aspect, the azole antifungal is miconazole, furconazole or itraconazole, or a pharmaceutically acceptable salt thereof. In a yet further aspect, the azole antifungal is itraconazole, or a pharmaceutically acceptable salt thereof. The azole type antifungal agent is a compound having antifungal activities and represents a compound comprising an imidazole ring or a triazole ring in its molecule, and it may, for example, be one or more selected from antifungal agents such as butoconazole or oxiconazole, clotrimazole, terconazole, econazole, tioconazole, miconazole, fluconazole, ketoconazole and itraconazole, disclosed in a literature such as Clinical Infectious Diseases, vol. 14 (Suppl 1), S161-9 (1992).

In a further aspect, the imidazole antifungal can be selected from clotrimazole, miconazole, econazole, oxyconazole, or a pharmaceutically acceptable salt thereof. In a still further aspect, the imidazole antifungal can be clotrimazole, or a pharmaceutically acceptable salt thereof. The imidazole compound that can be used includes, but is not limited to, 1-[(2-chlorophenyl)diphenylmethyl]-1H-imidazole, which is known as clotrimazole, 1-[2-[2,4-dichlorophenyl)-2-[(2,4-dichlorophenyl)methoxy]ethyl]-1H-imidazole, which is known as miconazole, 1-[2-[(4-chlorophenyl)methoxy]-2-(2,4-dichlorophenyl)ethyl]-1H-imidazole, which is known as econazole, 1-[2-(2,4-dichlorophenyl)2-[(2,6-dichlorophenyl)methoxy]ethyl]-1H-imidazole, which is known as isoconazole, 1-acetyl-4-[4-[[2-(2,4-dichlorophenyl)-2-(1H-imidazol-1-ylmethyl)-1,3-dioxolan-4-yl]methoxy]phenyl]piperazine, which is known as ketoconazole, 1-[2-(2,4-dichlorophenyl)-2-(2-propenyloxy)ethyl]-1H-imidazole, which is known as enilconazole, 1-[(1,1'-biphenyl)-4-ylphenylmethyl]-1H-imidazole, which is known as bifonazole, 1-[2-[(4-chlorophenylmethyl)thio]-2-(2,4-dichlorophenyl)ethyl]-1H-imidazole, which is known as sulconazole, 1-[2-[(2-chloro-3-thienyl)methoxy]-2-(2,4-dichlorophenyl)ethyl]-1H-imidazole, which is known as tioconazole, and 1-[2-(4-chlorophenyl)-2-[2,4-dichlorophenyl)methoxyimino] ethyl]-1H-imidazole, which is known as oxyconazole. These antifungal imidazole compounds can be used in the form of salt, such as hydrochloride, sulfate or nitrate.

The powder excipient base used in the disclosed pharmaceutical formulations can comprise a sugar alcohol, a non-ionic surfactant, or combinations thereof. Exemplary, but non-limiting sugar alcohols are xylitol, sorbitol, erythritol, or combinations thereof. The non-ionic surfactant can be a pharmaceutically acceptable poloxamer. "Poloxamers" refers to non-toxic, non-ionic triblock copolymers composed of a central hydrophobic chain of polyoxypropylene (poly (propylene oxide)) flanked by two hydrophilic chains of polyoxyethylene (poly(ethylene oxide)). It is further understood that poloxamers, or "PEO-PPO-PEO", are symmetrical triblock copolymers of polyoxyethylene (PEO, EO) and polyoxypropylene (PPO, PO) denoted as PEO-PPO-PEO or $(EO)n1(PO)m(EO)n2$ or $HO(C2H4O)a(C3H6O)b(C2H4O)cH$. These copolymers are commercially available and have been well characterized in the art. Examples are the poloxamers sold under various trademarks, such as Pluronic® (BASF Corp.) or Synperonics® (ICI). Further exemplary, but non-limiting, poloxamers include poloxamer 407, poloxamer 188, poloxamer 403 and the link. The poloxamer is present in a disclosed formulation in an amount to facilitate or allow solubilizing or stabilization in solution of the first antimicrobial agent, the second antimicrobial agent, and/or the third antimicrobial agent when utilized in a disclosed irrigation therapy solution.

In some aspects, a powder excipient base can comprise one or more sugar alcohols and one or more poloxamers. A commercially available suitable example of such a powder excipient base is LoxaSperse®.

Irrigation Therapy Solutions for Treatment of Diabetic Foot Ulcers

Disclosed herein are irrigation therapy solutions comprising a disclosed pharmaceutical formulation. The irrigation therapy solutions can be used for the treatment and/or prevention of diabetic foot ulcers. In various aspects, a disclosed irrigation therapy solution comprises about 1 gram to about 10 grams of a disclosed pharmaceutical composition dissolved in a volume of about 1.5 to about 5 liters of water. In a further aspect, a disclosed irrigation solution comprises about 2 gram to about 5 grams of a disclosed pharmaceutical composition is dissolved in a volume of about 2.5 to about 3.5 liters of water. In a still further aspect, a disclosed irrigation solution comprises about 2.8 gram to about 3.2 grams of a disclosed pharmaceutical composition is dissolved in a volume of about 2.8 to about 3.2 liters of water.

In some instances, for ease of patient use, it may be desirable to use a scoop designed to have a volume such that a level scoopful will measure the desired weight or mass of the pharmaceutical composition, based on the powder characteristics, e.g., granularity and powder density, of the pharmaceutical composition. That is, such a scoop can be designed to provide about 1 gram to about 10 grams, about 2 gram to about 5 grams, about 2.5 grams to about 3.5 grams, about 2.3 gram to about 3.8 grams, or about 2.8 gram to about 3.2 grams of a disclosed pharmaceutical composition in a level scoopful.

In some instances, the irrigation therapy solutions can be used with a suitable irrigation therapy delivery device. The irrigation therapy solutions are prepared as an aqueous solution in water, e.g., a sterile water, having a suitable pH, e.g., a pH between about 7.6 and 8.8. In some instances, the irrigation therapy solution has a pH of from about 8.5 to about 8.7. In some instances, the irrigation therapy solution can further comprise a hypochlorite solution, e.g., further comprise a Dakin's solution at a concentration of from about 0.050% to about 0.025%.

Wound Dressing Treatment Solutions

Disclosed herein are wound dressing treatment solutions comprising a disclosed pharmaceutical formulation. The wound dressing treatment solutions can be used with wound dressings, e.g., for the treatment and/or prevention of diabetic foot ulcers, other skin ulcers, or wound, including a chronic wound. In various aspects, a disclosed wound dressing treatment solution comprises about 1 gram to about 10 grams of a disclosed pharmaceutical composition dissolved in a volume of about 100 mL to about 1 liters of water or normal saline. In some instances, the water is sterile water or sterile standard saline. In a further aspect, a disclosed wound dressing solution comprises about 1 gram to about 5 grams of a disclosed pharmaceutical composition is dissolved in a volume of about 100 mL to about 500 mL of water or normal saline. In a still further aspect, a disclosed wound dressing solution comprises about 1 gram to about 2.5 grams of a disclosed pharmaceutical composition is dissolved in a volume of about 100 mL to about 500 mL of water or normal saline. In a yet further aspect, a disclosed wound dressing solution comprises about 1 gram to about 2 grams of a disclosed pharmaceutical composition is dissolved in a volume of about 100 mL to about 500 mL of water or normal saline. In an even further aspect, a disclosed wound dressing solution comprises about 1 gram to about 1.5 grams of a disclosed pharmaceutical composition is dissolved in a volume of about 100 mL to about 500 mL of water or normal saline.

In some instances, for ease of patient use, it may be desirable to use a scoop designed to have a volume such that a level scoopful will measure the desired weight or mass of the pharmaceutical composition, based on the powder characteristics, e.g., granularity and powder density, of the pharmaceutical composition. That is, such a scoop can be designed to provide about 1 gram to about 10 grams, about 1 gram to about 5 grams, about 1 gram to about 2.5 grams, about 1 gram to about 2 grams, or about 1 gram to about 1.5 grams of a disclosed pharmaceutical composition in a level scoopful.

In some instances, a disclosed wound dressing solution has a suitable pH, e.g., a pH between about 7.0 and 8.8. In a further aspect, the disclosed wound dressing solution has a pH of from about 7.2 to about 8.7. In a further aspect, the disclosed wound dressing solution has a pH of from about 7.2 to about 7.8.

In some instances, the disclosed wound dressing solution can further comprise a hypochlorite solution, e.g., further comprise a Dakin's solution at a concentration of from about 0.050% to about 0.025%.

Topical Treatment Solutions

Disclosed herein are topical treatment solutions comprising a disclosed pharmaceutical formulation. The topical treatment solutions can be used with wound dressings, e.g., for the treatment and/or prevention of diabetic foot ulcers, other skin ulcers, or wounds, including a chronic wounds. In various aspects, a disclosed topical treatment solution comprises about 0.1 gram to about 5 grams of a disclosed pharmaceutical composition dissolved in a volume of about 10 mL to about 100 mL of water or normal saline. In some instances, the water is sterile water or sterile standard saline. In a further aspect, a disclosed topical solution comprises about 0.1 gram to about 2.5 grams of a disclosed pharmaceutical composition is dissolved in a volume of about 10 mL to about 50 mL of water or normal saline. In a still further aspect, a disclosed topical solution comprises about 0.25 gram to about 1.5 grams of a disclosed pharmaceutical composition is dissolved in a volume of about 10 mL to about 30 mL of water or normal saline. In a yet further aspect, a disclosed topical solution comprises about 0.5 gram to about 1.5 grams of a disclosed pharmaceutical composition is dissolved in a volume of about 15 mL to about 30 mL of water or normal saline. In an even further aspect, a disclosed topical solution comprises about 0.7 gram to about 1.2 grams of a disclosed pharmaceutical composition is dissolved in a volume of about 15 mL to about 30 mL of water or normal saline.

In some instances, for ease of patient use, it may be desirable to use a scoop designed to have a volume such that a level scoopful will measure the desired weight or mass of the pharmaceutical composition, based on the powder characteristics, e.g., granularity and powder density, of the pharmaceutical composition. That is, such a scoop can be designed to provide about 0.1 gram to about 5 grams, about 0.1 gram to about 2.5 grams, about 0.25 gram to about 1.5 grams, about 0.5 gram to about 1.5 grams, or about 0.7 gram to about 1.2 grams of a disclosed pharmaceutical composition in a level scoopful.

In some instances, a disclosed topical solution has a suitable pH, e.g., a pH between about 7.0 and 8.8. In a further aspect, the disclosed topical solution has a pH of from about 7.2 to about 8.7. In a further aspect, the disclosed topical solution has a pH of from about 7.2 to about 7.8.

In some instances, the disclosed topical solution can further comprise a hypochlorite solution, e.g., further comprise a Dakin's solution at a concentration of from about 0.050% to about 0.025%.

Methods of Treating Diabetic Foot Ulcers

The present disclosure also pertains to methods for the treatment of diabetic foot ulcers, comprising administering to a subject an effective amount of a disclosed irrigation therapy solution, wherein the subject is diagnosed with diabetes; wherein the disclosed irrigation therapy solution is contained in a suitable irrigation therapy delivery device; and wherein administering comprises the subject placing at least one foot in the irrigation therapy delivery device for a suitable period of time. The subject may be suffering from Type I diabetes or Type II diabetes, and has a foot ulcer, defined as an open wound anywhere on the foot (heel, mid-foot, and forefoot).

As used herein, "treating" a diabetic foot ulcer includes (a) limiting the progression in size, area, and/or depth of the foot ulcer;

(b) reducing size, area, and/or depth of the foot ulcer;

(c) increasing rate of healing and/or reducing time to healing;

(d) healing of the foot ulcer (100% epithelialization with no drainage); and (e) decreased incidence of amputation or slowing in time to amputation.

Treatment of diabetic foot ulcers has a main objective of closing the wound; preferably, ulcers should be treated in a preliminary step in order to allow an early cure.

There are several types and grades of diabetic ulcers depending on foot damage. Ulcers are commonly located on foot sole and rarely above foot. There is not any universally accepted classification encompassing assessment criteria of diabetic foot lesions; however, the most common classification is Wagner scale which assesses ulcer depth together with the presence of gangrene and perfusion loss by using six grades (0-5). Table 1 shows the classification according to Wagner scale.

TABLE 1

Classification of diabetic foot ulcers according to Wagner scale.

| Grade (Wagner Scale) | Lesion | Characteristics |
| --- | --- | --- |
| 0 | None - foot at risk | Callus, hallux, mallet toes |
| 1 | Surface ulcers | Destruction of full skin thickness |
| 2 | Deep ulcer | Penetrates skin, fat and ligaments without affecting bone, infected |
| 3 | Deep ulcers plus abscess (osteomyelitis) | Extensive and deep, secretion, bad odor |
| 4 | Limited gangrene | Necrosis in a section of the foot |
| 5 | Extended gangrene | Whole foot affected; systemic effects |

The foot ulcer may be caused by any underlying pathology, including but not limited to diabetes, neuropathy (including, but not limited to, diabetic neuropathy), trauma, deformity, high plantar pressures, callus formation, edema, and peripheral arterial disease. In a further aspect, the foot ulcer can be a diabetic foot ulcer, such as a diabetic foot ulcer caused, at least in part, by neuropathy and resulting pressure (weight bearing on the extremity due to lack of feeling in the foot). Human diabetic foot ulcers are frequently associated with neuropathy and pressure. In a further preferred aspect, the diabetic foot ulcer can comprise one or more calluses.

In a further aspect, the diabetic foot ulcer is a chronic ulcer. As used herein, a "chronic" foot ulcer is one that has been present for at least 7 days with no reduction in size; preferably at least 14 days; even more preferably, present at least 21 or 28 days with no reduction in size. In a further preferred aspect that can be combined with any of these aspects, the chronic foot ulcer has not responded (i.e., no reduction in size, area, and/or depth of the foot ulcer; no healing of the foot ulcer) to any other treatment.

In various aspects, disclosed herein are methods of treating and/or preventing diabetic foot ulcers, other skin ulcers, or other wounds comprising applying a wound dressing comprising a wound dressing substrate comprising a disclosed wound dressing treatment solution. The wound dressing treatment solution is prepared as described herein above.

The wound dressing substrate may be selected from wound dressing hydrogels and wound dressing fabrics. These are each generally known in the art, and, as used herein, the term "wound dressing" as modifying "hydrogels" and "fabrics" is to be understood as connoting that the hydrogels and fabrics are suitable for dressing a wound.

A hydrogel is formed by creating a cross-linked network of polymer chains. The polymer used to form a hydrogel that is used to form a wound dressing of the present invention can be virtually any "hydrogel polymer", which is to be understood herein as any natural or synthetic polymer suitable for making a wound dressing hydrogel. Specific examples of polymers that can be used include polyvinyl alcohol, alginate, chitosan, carboxyethyl chitosan, methylcellulose, gelatin, soy protein, wheat protein, xanthan gum, gum arabic, polyacrylamide, and other polyalcohols, polysaccharides, polyamines, proteins, or mixtures thereof.

In some aspects, the wound dressing hydrogel is formed of combinations of two or more polymers such as alginate-gelatin, alginate-chitosan, alginate-methylcellulose, alginate-polyethylene glycol, and soy protein-chitosan.

Wound dressing fabrics are generally known and are generally woven or non-woven fabrics formed of woven or non-woven natural or synthetic fibers. The wound dressing fabrics employed in this invention may be virtually any fabric known or later discovered as being suitable for making a wound dressing. Specific examples of fabrics include those woven or non-woven fabrics formed of fibers selected from vegetable fibers such as cotton, hemp, jute, and flax; and synthetic fibers such as cellulose-derived synthetic fibers (e.g., rayon, modal) and polymer-based fibers such as nylon, polyester, polyacrylonitrile, polymethyl methacrylate, polyethylene, polypropylene, and other acrylics and polyolefins.

In some aspects, the wound dressing fabric is a gauze-type fabric formed of cotton, silk, paraffin tulle, nylon, polyester, polyethylene, or mixtures thereof. In other aspects, electrospun nanofibers such as those of gelatin and carboxyethyl chitosan-polyvinyl alcohol mixture can be mixed with the other thicker fibers in a wound dressing gauze-type fabric.

In various aspects, the term "wound dressing substrate" used herein is taken to include any pharmaceutically acceptable wound covering or support matrix such as: (a) a gauze-type fabric as described herein; (b) films, including those of a semipermeable or a semi-occlusive nature such as polyurethane copolymers, acrylamides, acrylates, paraffin, polysaccharides, cellophane and lanolin; (c) hydrocolloids including carboxymethylcellulose protein constituents of gelatin, pectin, and complex polysaccharides including Acacia gum, guar gum and karaya. These materials may be utilized in the form of a flexible foam or, in the alternative, formulated in polyurethane or, in a further alternative, formulated as an adhesive mass such as polyisobutylene; (d) hydrogels such as agar, starch or propylene glycol; which typically contain about 80% to about 90% water and are conventionally formulated as sheets, powders, pastes and gels in conjunction with cross-linked polymers such as polyethylene oxide, polyvinyl pyrrolidone, acrylamide, propylene glycol; (e) foams such as polysaccharide which consist of a hydrophilic open-celled contact surface and hydrophobic closed-cell polyurethane; (f) impregnates including pine mesh gauze, paraffin and lanolin-coated gauze, polyethylene glycol-coated gauze, knitted viscose, rayon, and polyester; and (g) cellulose-like polysaccharide such as alginates, including calcium alginate, which may be formulated as non-woven composites of fibers or spun into woven composites.

In various aspects, the disclosed wound dressing is applied to a diabetic foot ulcer, other skin ulcer, or wound, including a chronic wound. The disclosed wound dressing can further comprise or be covered with a non-adherence wound dressing comprising knitted cellulose acetate fabric and impregnated with a petrolatum emulsion, e.g., ADAPTIC™ Non-Adhering Dressing. The inclusion of a non-adherence wound dressing can be useful to prevent the disclosed wound dressing from quickly drying out and/or mitigation of wound dressing adherence to the ulcer or wound, including a chronic wound, site. In the disclosed methods of treating and/or preventing diabetic foot ulcers, other skin ulcers, or other wounds, the disclosed wound dressing can be change from about 6 times daily to a once per 72 hours. In a further aspect, in the disclosed methods of treating and/or preventing diabetic foot ulcers, other skin ulcers, or other wounds, the disclosed wound dressing can be change from about 3 times daily to a once per 72 hours.

In a further aspect, disclosed herein are methods of preparing a disclosed wound dressing comprising incorporating into a wound dressing substrate such as, but not limited to, dressing fabrics and hydrogels. In other aspects, a wound dressing substrate can comprise solid films, porous foams (e.g., those made of polyurethane or other polymers), porous membranes, creams, meshes, and gauzes. As understood herein, "incorporating into a wound dressing substrate" can comprise incorporation by placing or immersing a wound dressing substrate in a disclosed wound dressing solution until essentially at equilibrium with the wound dressing solution, e.g., by placing or immersing for a period of about 1 minute to about 24 hours, or longer. In some instances, a wound dressing substrate can be packaged in sealed, single use sterile packaging comprising the wound dressing substrate in contact with the disclosed wound dressing solution.

Also disclosed herein are methods of treating and/or preventing diabetic foot ulcers, other skin ulcers, or wound, including a chronic wound, comprising or applying disclosed topical treatment solutions to an ulcer or wound site. For example, after a disclosed topical treatment solution is prepared, it can be transferred from a mixing container to a spray bottle capable of dispensing the disclosed topical treatment solution as a fine mist or spray comprising the topical treatment solution as an aerosol or a spray comprising fine droplets of the topical treatment solution. An ulcer or wound site can be provided a mist or spray of the disclosed topical treatment solution using the spray bottle until the ulcer or wound site is moist. The spray treatment can be applied about 1 time to about 10 times daily, in some instances from about once to twice daily. Following the spray treatment, the ulcer or wound site can be further provided with a suitable wound dressing.

The disclosed methods can further comprise debridement in and around the wound in combination with administration of the peptide and formulations thereof. Debridement of all necrotic, callus, and fibrous tissue is typically carried out for treatment of diabetic foot ulcers. Unhealthy tissue is sharply debrided back to bleeding tissue to allow full visualization of the extent of the ulcer and to detect underlying abscesses or sinuses. Any suitable debridement technique can be used, as determined by an attending physician. The wound can then be thoroughly flushed with sterile saline or a non-cytotoxic cleanser following debridement.

The disclosed methods of treating a diabetic foot ulcer not only decreases the average time for ulcer cure in patients with diabetic foot, but further prevents development thereof and decreases the possibility of appearance of future ulcers.

Kits

The present disclosure also pertains to kits for the treatment and/or prevention of diabetic foot ulcers, other skin ulcers, or wounds, including a chronic wounds.

The disclosed pharmaceutical formulations, the disclosed irrigation therapy solutions, the disclosed wound dressing treatment solutions, and the topical treatment solutions can conveniently be presented as a kit, whereby the disclosed formulations and solutions, with additional ingredients such as one or more antiseptic solution and further active or inactive ingredients, carriers, diluents, and the like, are provided with instructions for preparation of the actual dosage form, e.g., a disclosed solution, by the patient or person administering the drug to the patient. Such kits may be provided with all necessary materials and ingredients contained therein, or they may contain instructions for using or making materials or components that must be obtained independently by the patient or person administering the drug to the patient. In further aspects, a kit can include optional components that aid in the administration of the unit dose to patients, such as vials for reconstituting powder forms, syringes for injection, customized delivery systems, e.g., an irrigation therapy delivery device, sterile water and/or sterile saline, measuring containers, and the like. Additionally, a kit can contain instructions for preparation and administration of the disclosed solutions. The kit can be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

In a further aspect, the disclosed kits can be packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. The present invention also features such kits further containing instructions for use.

In a further aspect, the present disclosure also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

In various aspects, the disclosed kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using or treating, and/or the disclosed pharmaceutical formulations.

In various aspects, the present disclosure relates to kits comprising a disclosed formulation; and one or more of: (a) instructions for treating a diabetic foot ulcer; (b) instructions for preventing a diabetic foot ulcer; (c) instructions for preparation of an irrigation therapy solution for treating a diabetic foot ulcer; (d) instructions for preparation of an irrigation therapy solution for preventing a diabetic foot ulcer; or (e) an irrigation therapy delivery device for circulating an aqueous solution comprising the pharmaceutical formulation for use in treating or preventing a diabetic foot ulcer.

In various aspects, the present disclosure relates to kits comprising a disclosed formulation; and one or more of: (a) instructions for treating a diabetic foot ulcer; (b) instructions for preventing a diabetic foot ulcer; or (c) an irrigation therapy delivery device for circulating an aqueous solution comprising the pharmaceutical formulation for use in treating or preventing a diabetic foot ulcer.

In a further aspect, the present disclosure relates to kits comprising a disclosed pharmaceutical formulation, and one or more of: (a) an antiseptic composition or solution; (b) water or standard saline; (c) a measuring container for measuring and dispensing a known quantity of the pharmaceutical formulation; (d) a measuring container for measuring and dispensing a known quantity of the antiseptic solution; (e) a measuring container for measuring and dispensing a known volume of water or standard saline; (f) an irrigation therapy delivery device; (g) instructions for treating a wound or ulcer; or (h) instructions for preparing an irrigation therapy in connection with treating a wound or ulcer.

In a further aspect, the present disclosure relates to kits comprising a disclosed pharmaceutical formulation, and one or more of: (a) a wound dressing substrate; (b) an antiseptic composition or solution; (c) water or standard saline; (d) a measuring container for measuring and dispensing a known quantity of the pharmaceutical formulation; (e) a measuring container for measuring and dispensing a known quantity of the antiseptic solution; (f) a measuring container for measuring and dispensing a known volume of water or standard saline; (g) instructions for preparing a wound dressing comprising the wound dressing substrate and a wound dressing treatment solution; or (g) instructions for treating a wound or ulcer using a wound dressing comprising the wound dressing substrate and a wound dressing treatment solution.

In a further aspect, the present disclosure relates to kits comprising a disclosed pharmaceutical formulation, and one or more of: (a) an antiseptic composition or solution; (b) water or standard saline; (c) a measuring container for measuring and dispensing a known quantity of the pharmaceutical formulation; (d) a measuring container for measuring and dispensing a known quantity of the antiseptic solution; (e) a measuring container for measuring and dispensing a known volume of water or standard saline; (f) a topical treatment solution dispensing device, e.g., a spray bottle; (g) instructions for preparing a topical treatment solution; or (g) instructions for treating a wound or ulcer using a topical treatment solution.

In a further aspect, the present disclosure relates to kits comprising a disclosed irrigation therapy solutions comprising a disclosed pharmaceutical formulation, and one or more of: (a) an antiseptic composition or solution; (b) a measuring container for measuring and dispensing a known quantity of the irrigation therapy solution; (c) a measuring container for measuring and dispensing a known quantity of the antiseptic solution; (d) an irrigation therapy delivery device; (e) instructions for treating a wound or ulcer; or (f) instructions for preparing an irrigation therapy in connection with treating a wound or ulcer.

In a further aspect, the present disclosure relates to kits comprising a wound dressing treatment solution, and one or more of: (a) a wound dressing substrate; (b) an antiseptic composition or solution; (c) water or standard saline; (d) a measuring container for measuring and dispensing a known quantity of the wound dressing treatment solution; (e) a measuring container for measuring and dispensing a known quantity of the antiseptic solution; (f) a measuring container for measuring and dispensing a known volume of water or standard saline; (g) instructions for preparing a wound dressing comprising the wound dressing substrate and a wound dressing treatment solution; or (h) instructions for treating a wound or ulcer using a wound dressing comprising the wound dressing substrate and a wound dressing treatment solution.

In a further aspect, the present disclosure relates to kits comprising a disclosed topical treatment solution, and one or more of: (a) an antiseptic composition or solution; (b) water or standard saline; (c) a measuring container for measuring and dispensing a known quantity of the pharmaceutical formulation; (d) a measuring container for measuring and dispensing a known quantity of the antiseptic solution; (e) a measuring container for measuring and dispensing a known volume of water or standard saline; (f) a topical treatment solution dispensing device, e.g., a spray bottle; or (g) instructions for treating a wound or ulcer using a topical treatment solution.

In various aspects, the measuring container for measuring and dispensing a known quantity of the pharmaceutical formulation. That is, the measuring container can be a scoop designed to have a volume such that a level scoopful or based on indicated markings thereon will measure the desired weight or mass of the pharmaceutical composition, based on the powder characteristics, e.g., granularity and powder density, of the pharmaceutical composition. The measuring container, e.g., a scoop, can be designed to provide a desired weight or mass of a disclosed pharmaceutical formulation to be dispensed into a specified volume of water or standard saline.

In various aspects, the water or standard saline in the kit can be a sterile solution. It can be packaged in a specified volume to which is added a specified amount, e.g., weight or mass of a disclosed pharmaceutical formulation, and mixed until complete dissolution of the disclosed pharmaceutical formulation therein. In some instances, the water or standard saline in the kit can be packaged such that it comprises an outlet that can be opened and closed by a patent or other person preparing a disclosed solution. As such, the water or standard saline can be dispensed into a measuring container, e.g., a disposable graduated cylinder with markings thereon, to obtain a desired volume of the water or standard saline into which to mix a desired amount of the pharmaceutical formulation.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1. Exemplary Disclosed Pharmaceutical Formulation

A representative disclosed pharmaceutical formulation comprises:
- Tobramycin sulfate, 24 wt % (wt % based on tobramycin activity)
- Vancomycin HCl, 30 wt % (wt % based on vancomycin activity)
- Itraconazole, 8 wt %
- Loxasperse®, 32 wt %

In the present example, the Certificate of Analysis data indicated: (a) tobramycin activity was 727 μg per mg total weight; and (b) vancomycin activity was 1085 μg per mg total weight.

Briefly, the procedure for preparation of powder formulation was as follows:
- weigh out 8 grams of itraconazole plus or minus 3 percent and leave in weigh boat;
- weigh out 31.34 grams of Loxasperse®;
- to a mixing jar or mortar, add the 8 grams of itraconazole and approximately 8 grams of Loxasperse®, then mix the products together—mixing can be carried out by hand or by using an unguator set on medium speed for about 5 minutes;
- weigh out 27.65 grams of vancomycin HCl plus or minus 3% and leave in weigh boat (which is equivalent to 30 grams of vancomycin activity based on the Certificate of Analysis);
- weigh out 33.01 grams of tobramycin sulfate plus or minus 3% and leave in weigh boat (which is equivalent to 24 grams of tobramycin activity based on the Certificate of Analysis);
- add the remaining Loxasperse® (about 23 grams) to the itraconazole and Loxasperse® mixture prepared above, and mix by hand until well-mixed;
- add the foregoing mixture to a 250 gram unguator jar along with the vancomycin and tobramycin, followed by mixing on medium speed for 10 minutes; and
- package in an in light resistant air tight container.

The foregoing mixture is formulated such that 3 grams of the complete powder mixture should be dispensed in about 3 liters of water. Dispensing can be carried out using a dry powder scoop sized to measure out about 3 grams of powder. The amount of 3 grams of the complete powder mixture in about 3 liters of water is nominally a single irrigation therapy treatment dose. The pH of the 3 grams of complete powder mixture dispensed in about 3 liters of water was about 8.5 to 8.7.

Example 2. Clinical Study

The exemplary disclosed pharmaceutical formulation of Example 1 can be assessed in an appropriate clinical study such as the prospective study described herein. The study participants in the study must be diagnosed with diabetes type 1 or 2 with a documented open diabetic foot ulcer/wound with or without a secondary fungal infection. Healing rates are evaluated every two weeks following the initiation of study therapy up to three months. Participants are treated with a disclosed pharmaceutical formulation, e.g., the formulation of Example 1, in anti-infective irrigation daily therapy until closure of the ulcer or up to a maximum of 3 months.

A sample size of approximately 100 patients is estimated to have 90% power to detect 15% improvement in ulcer healing rate 45% and 35% compared to historical benchmarks of 30% for ulcers of less than 6 months duration and 20% for ulcers greater than 6 months duration. For example, it has been reported (see Advance in Wound Care, Volume 7, Number 3 entitled Publicly Reported Wound Healing Rates: The fantasy and the Reality) that at 12 weeks, about 30% of DFU's were healed. The foregoing report examined the change in 71,957 DFUs over a 4-week period as a predictor of wound healing within 12 weeks.

The purpose of the study described herein is to evaluate the effectiveness of a disclosed pharmaceutical formulation used in anti-infective irrigation therapy to increase the healing rates of diabetic foot ulcers. Specifically, a study goal is to measure the healing rate of 100 patients known to have diabetes type 1 or 2 who have ulcers/open wounds on their feet with or without a fungal infection. Each participant is provided the disclosed pharmaceutical formulation, e.g., that of Example, along with a suitable irrigation therapy delivery device. Participants are instructed in detail on the procedure of how to mix the disclosed pharmaceutical formulation for irrigation therapy and are asked to soak their foot/feet in the irrigation therapy delivery device once daily for 10 minutes for a minimum of 4 weeks and maximum of 3 months depending on how they respond to treatment.

In the study described herein, the following endpoints are assessed: (a) a primary endpoint, which can be the percent change in wound area by planimetry, stratified by pre-treatment ulcer duration greater than 6 months or prior treatment failure; and (b) one or more secondary endpoints, which can comprise: (i) the determination of the change in University of Texas Wound classification from baseline at 4 weeks, 8 weeks, and 12 weeks; (ii) the percentage of patients with would closure at 12 weeks stratified by pre-treatment ulcer duration greater than 6 months or prior treatment failure with complete wound healing be defined as 100% re-epithelialization of the wound surface with absence of drainage in accordance with the Wound Healing Society definition; and (iii) healing rates of any diagnosed secondary infection that may be present on the foot, including, but not limited to, tinea pedis and/or onychomycosis.

The study described herein also monitors for potential adverse events including, but not limited to, clinical worsening as determined by the study physician and/or delivery device and/or irrigation related complications.

The present disclosure further includes the following embodiments.

1A. A pharmaceutical composition comprising:
   a. a first antimicrobial agent, a second antimicrobial agent, a third antimicrobial agent, and a powder excipient base;
   b. wherein the first antimicrobial agent is an aminoglycoside antibiotic or a fluoroquinolone, and is present in an amount of from about 15 wt % to about 35 wt %;
   c. wherein the second antimicrobial agent is glycopeptide antibiotic, and is present in an amount of from about 15 wt % to about 40 wt %;
   d. wherein the third antimicrobial agent is an azole antifungal or an imidazole antifungal, and is present in an amount of from about 1 wt % to about 15 wt %;
   e. wherein the powder excipient base is present in an amount of from about 10 wt % to about 50 wt %;
   f. wherein the wt % is based on the total weight of the first antimicrobial agent, the second antimicrobial agent, the third antimicrobial agent, and the powder excipient base such that the total wt % for foregoing components is 100 wt %; and
   g. wherein the first antimicrobial agent, the second antimicrobial agent, the third antimicrobial agent, and the powder excipient base are a homogeneously dispersed powder mixture.

2A. The pharmaceutical composition of paragraph 1A, wherein the first antimicrobial agent is an aminoglycoside antibiotic.

3A. The pharmaceutical composition of paragraph 2A, wherein the aminoglycoside antibiotic is tobramycin, or a pharmaceutically acceptable salt thereof.

4A. The pharmaceutical composition of paragraph 1A, wherein the first antimicrobial agent is a fluoroquinolone.

5A. The pharmaceutical composition of paragraph 4A, wherein the fluoroquinolone is ciprofloxacin, or a pharmaceutically acceptable salt thereof.

6A. The pharmaceutical composition of any one of paragraphs 1A-5A, wherein the second antimicrobial agent is vancomycin, or a pharmaceutically acceptable salt thereof.

7A. The pharmaceutical composition of any one of paragraphs 1A-6A, wherein the third antimicrobial agent is an azole antifungal.

8A. The pharmaceutical composition of paragraph 7A, wherein the azole antifungal is itraconazole, or a pharmaceutically acceptable salt thereof.

9A. The pharmaceutical composition of any one of paragraphs 1A-6A, wherein the third antimicrobial agent is an imidazole antifungal.

10A. The pharmaceutical composition of paragraph 7A, wherein the imidazole antifungal is clotrimazole, or a pharmaceutically acceptable salt thereof.

11A. The pharmaceutical composition of any one of paragraphs 1A-10A, wherein the first antimicrobial agent is present in an amount of from about 20 wt % to about 30 wt %.

12A. The pharmaceutical composition of paragraph 11A, wherein the first antimicrobial agent is present in an amount of from about 20 wt % to about 25 wt %.

13A. The pharmaceutical composition of any one of paragraphs 1A-12A, wherein the second antimicrobial agent is present in an amount of from about 25 wt % to about 40 wt %.

14A. The pharmaceutical composition of paragraph 13A, wherein the second antimicrobial agent is present in an amount of from about 25 wt % to about 35 wt %.

15A. The pharmaceutical composition of any one of paragraphs 1A-14A, wherein the third antimicrobial agent is present in an amount of from about 5 wt % to about 10 wt %.

16A. The pharmaceutical composition of paragraph 15A, wherein the third antimicrobial agent is present in an amount of from about 7 wt % to about 9 wt %.

17A. The pharmaceutical composition of any one of paragraphs 1A-16A, wherein the powder excipient base comprises a sugar alcohol, a non-ionic surfactant, or combinations thereof.

18A. The pharmaceutical composition of paragraph 17A, wherein the sugar alcohol comprises xylitol, sorbitol, erythritol, or combinations thereof.

19A. The pharmaceutical composition of paragraph 17A or 18A, wherein the non-ionic surfactant is a nonionic tri-block copolymer comprising a central hydrophobic chain of polyoxypropylene flanked by two hydrophilic chains of polyoxyethylene.

20A. An irrigation therapy composition comprising about 1 gram to about 10 grams of the pharmaceutical composition any one of paragraphs 1-19 dissolved in a volume of about 1.5 to about 5 liters of water.

21A. The irrigation therapy solution of paragraph 20A, wherein the pH of the aqueous solution is about 7.5 to about 8.8.

22A. The irrigation therapy solution of paragraph 21A, wherein the pH of the aqueous solution is about 8.2 to about 8.8.

23A. The irrigation therapy solution of any one paragraphs 20A-22A, wherein about 2 gram to about 5 grams of the pharmaceutical composition is dissolved in a volume of about 2.5 to about 3.5 liters of water.

24A. The irrigation therapy solution of any one of paragraphs 20A-23A, further comprising from about 0.050% to about 0.200% Dakin's solution.

25A. A method for the treatment of diabetic foot ulcers, comprising administering to a subject an effective amount of the irrigation therapy solution of any one of paragraphs 20A-24A,
   a. wherein the subject is diagnosed with diabetes;
   b. wherein the irrigation therapy solution of any one of paragraphs 20-24 is contained in a suitable irrigation therapy delivery device;
   c. wherein administering comprises the subject placing at least one foot in the irrigation therapy delivery device for a suitable period of time.

26A. The method of paragraph 25A, wherein the irrigation therapy delivery device maintains the irrigation therapy solution at a suitable temperature.

27A. The method of paragraph 25A or 26A, wherein the irrigation therapy delivery device circulates the irrigation therapy solution.

28A. The method of paragraph 25A, wherein the method further comprises the step of identifying whether the subject is need of treatment of a diabetic foot ulcer.

29A. The method of paragraph 25A, wherein the method further comprises the step of identifying whether the subject is need of preventing a diabetic foot ulcer.

30A. The method of paragraphs 28A or 29A, wherein the diabetic foot ulcer is one caused, at least in part, by neuropathy and resulting pressure.

31A. The method of any one of paragraphs 28A-30A, wherein the diabetic foot ulcer comprises one or more calluses.

32A. The method of any one of paragraphs 28A-31A, wherein the diabetic foot ulcer is a chronic ulcer.

33A. The method of any one of paragraphs 28A-32A, wherein the diabetic foot ulcer has not responded to prior treatment of the diabetic foot ulcer.

34A. The method of any one of paragraphs 28A-32A, wherein the diabetic foot ulcer has responded only partially to prior treatment of the diabetic foot ulcer.

35A. A kit comprising the pharmaceutical formulation of any one of paragraphs 1A-19A; and one or more of:
 a. instructions for treating a diabetic foot ulcer;
 b. instructions for preventing a diabetic foot ulcer;
 c. instructions for preparation of an irrigation therapy solution for treating a diabetic foot ulcer;
 d. instructions for preparation of an irrigation therapy solution for preventing a diabetic foot ulcer; or
 e. an irrigation therapy delivery device for circulating an aqueous solution comprising the pharmaceutical formulation for use in treating or preventing a diabetic foot ulcer.

36A. A kit comprising the irrigation therapy solution of any one of paragraphs 20A-24A; and one or more of:
 a. instructions for treating a diabetic foot ulcer;
 b. instructions for preventing a diabetic foot ulcer; or
 c. an irrigation therapy delivery device for circulating an aqueous solution comprising the pharmaceutical formulation for use in treating or preventing a diabetic foot ulcer.

It should be emphasized that the above-described aspects of the present disclosure are merely possible examples of implementations set forth for a clear understanding of the principles of the disclosure. Many variations and modifications may be made to the above-described aspect(s) without departing substantially from the spirit and principles of the disclosure. All such modifications and variations are intended to be included herein within the scope of this disclosure and protected by the following claims.

What is claimed is:

1. A method for the treatment of diabetic foot ulcers using water-soluble anti-infective medication, comprising administering to a subject an effective amount of an irrigation therapy solution consisting of about 1 gram to about 10 grams of a pharmaceutical composition dissolved in a volume of about 1.5 to about 5 liters of water,
 wherein the pharmaceutical composition comprises:
 a first antimicrobial agent, a second antimicrobial agent, a third antimicrobial agent, and a powder excipient base;
 wherein the first antimicrobial agent is an aminoglycoside antibiotic or a fluoroquinolone, and is present in an amount of from about 15 wt % to about 35 wt %;
 wherein the second antimicrobial agent is glycopeptide antibiotic, and is present in an amount of from about 15 wt % to about 40 wt %;
 wherein the third antimicrobial agent is an azole antifungal or an imidazole antifungal, and is present in an amount of from about 1 wt % to about 15 wt %;
 wherein the powder excipient base is present in an amount of from about 10 wt % to about 50 wt %;
 wherein the wt % is based on the total weight of the first antimicrobial agent, the second antimicrobial agent, the third antimicrobial agent, and the powder excipient base such that the total wt % for foregoing components is 100 wt %; and
 wherein the first antimicrobial agent, the second antimicrobial agent, the third antimicrobial agent, and the powder excipient base are a homogeneously dispersed powder mixture prior to being dissolved;
 wherein the subject is diagnosed with diabetes;
 wherein the irrigation therapy solution is contained in a suitable irrigation therapy delivery device;
 wherein administering comprises the subject placing at least one foot in the irrigation therapy delivery device for a suitable period of time.

2. The method of claim 1, wherein the first antimicrobial agent is an aminoglycoside antibiotic.

3. The method of claim 2, wherein the aminoglycoside antibiotic is tobramycin, or a pharmaceutically acceptable salt thereof.

4. The method of claim 1, wherein the second antimicrobial agent is vancomycin, or a pharmaceutically acceptable salt thereof.

5. The method of claim 1, wherein the third antimicrobial agent is an azole antifungal.

6. The method of claim 5, wherein the azole antifungal is itraconazole, or a pharmaceutically acceptable salt thereof.

7. The method of claim 1, wherein the first antimicrobial agent is present in the pharmaceutical composition in an amount of from about 20 wt % to about 30 wt %.

8. The method of claim 1, wherein the pH of the aqueous solution is about 7.5 to about 8.8.

9. The method of claim 8, wherein the pH of the aqueous solution is about 8.2 to about 8.8.

10. The method of claim 1, wherein about 2 gram to about 5 grams of the pharmaceutical composition is dissolved in a volume of about 2.5 to about 3.5 liters of water.

11. The method of claim 1, wherein the irrigation therapy delivery device maintains the irrigation therapy solution at a suitable temperature.

12. The method of claim 1, wherein the irrigation therapy delivery device circulates the irrigation therapy solution.

13. The method of claim 1, wherein the method further comprises the step of identifying whether the subject is need of treatment of a diabetic foot ulcer.

14. The method of claim 1, wherein the method further comprises the step of identifying whether the subject is need of preventing a diabetic foot ulcer.

15. The method of claim 1, wherein the diabetic foot ulcer has responded only partially to prior treatment of the diabetic foot ulcer.

* * * * *